United States Patent [19]

Montone

[11] Patent Number: 5,156,587
[45] Date of Patent: Oct. 20, 1992

[54] METHOD FOR TREATING MALIGNANT CELLS

[76] Inventor: Liber J. Montone, 9242 Vanderbilt Dr., Naples, Fla. 33963

[21] Appl. No.: 3,782

[22] Filed: Jan. 9, 1987

Related U.S. Application Data

[63] Continuation-in-part of Ser. No. 528,442, Sep. 1, 1983, abandoned.

[51] Int. Cl.$^5$ ............................................. A61N 2/04
[52] U.S. Cl. ................................................... 600/13
[58] Field of Search ...................... 128/1.3, 1.5; 600/9, 600/13, 15

[56] References Cited

FOREIGN PATENT DOCUMENTS 506966  8/1978  U.S.S.R. ................................ 128/1.5
1595108 8/1981  United Kingdom ................. 128/1.5

OTHER PUBLICATIONS

Lenzi, Radiology, Sep. 1940, pp. 307–314.
Barnothy, Medical Physics, vol. 3, 1960, pp. 61–62.
Mansfield et al., NMR Imaging in Biomedicine, Sup. 2, Academic Press, N.Y., 1982.
Harrison's Principles of Internal Medicine, 10th Ed., McGraw Hill, N.Y., 1983, pp. 834 and 1761–1762.
Cramp, I-ON-A CO—The Magic Horse Collar, reprint from Gygeia, Feb. 1927.
Solov'eva et al., Biomdeical Engr., vol. 7, No. 5, p. 2914, Sep.–Oct., 1973.

*Primary Examiner*—Lee S. Cohen
*Attorney, Agent, or Firm*—Gregory E. Montone

[57] ABSTRACT

A method and apparatus for destroying or retarding growth of malignant cells and tumors using one or more coils of wire, externally applied to the body, for chosen periods, which are connected to an alternating current source to produce a low frequency sinusoidal magnetic field of desired intensity at the irradiated malignant region to be treated.

21 Claims, 4 Drawing Sheets

METHOD FOR TREATING MALIGNANT CELLS

This application is a continuation-in-part of application Ser. No. 528,442, filed Sep. 1, 1983, now abandoned.

BACKGROUND OF THE INVENTION

1. Field To Which Invention Relates

This invention for medical profession use relates to a method and apparatus for treatment of malignant cells and tumors and, in particular, to a method and apparatus for treating such malignant cells and tumors by irradiating them with energy from the low frequency end of the electromagnetic spectrum rather than from the traditional upper high frequency radiation therapy end of the spectrum thus subjecting the malignant cells and tumors to the influences of sinusoidal magnetic field of sufficient magnitude, applied for specific periods, to disturb them enough to attenuate or terminate the uncontrolled proliferation of abnormal cells.

2. The Prior Art

Radiation therapy for the treatment of some of the over one hundred different presently known human cancers has been effectively used by the medical profession for most of this century. This bombardment from x-ray tubes or radioactive materials of upper spectrum fringe electromagnetic wave energy is credited with greatly increasing the number of cancer regressions or cures. While radiation therapy may be the sole accepted treatment for some cancers, it is more generally used in conjunction with surgical measures and chemotherapy.

In spite of the long term use of this therapy, the mechanisms by which it works are not known. What is well known and empirically established is that some types of malignant cells are less resistant to the destructive forces of x-ray frequency radiation than the older normal cells. Therefore, the malignant cells are subjected to enough empirically established radiation to destroy the more sensitive malignant cells while the more resistant adjacent normal cells remain comparatively uninjured by the particular exposure. The cumulative effects of this form of energy, however, lower the resistance levels of normal cells and maximum x-ray exposure dosages result. Because of this, if complete regression of the malignant tumor being irradiated has not been achieved before the maximum dosage of radiation is reached, a grave, if not fatal, situation exists. When this situation occurs, this otherwise very effective therapy can no longer be used, and prior alternatives are dangerous and questionable. Unfortunately, this situation where maximum radiation exposure is reached before satisfactory regression is quite common in especially lethal forms of sarcomas and carcinomas. Accordingly, the present invention is directed to providing an alternative form of treatment which will attain good regression or destruction of such malignant cell formations without the above-noted cumulative effects found in conventional radiation treatment.

The state-of-the-art involving the use of magnetic fields for treating human type malignancies is relatively new and narrow. Prior to the present invention, the concentration of effort regarding magnetic field effects on malignant cells has been with the use of permanent magnets, direct current electromagnets and massive kilogauss unidirectional pulses electromagnets. The magnet field effects were first evaluated on laboratory animals which hosted human cancers. The results indicated that killer type tumors progressed slower in the presence of strong magnetic fields than similar cancers not subjected to the fields. Since the results were considered beneficial, a small number of people with terminal inoperable tumors were treated in Boston, Mass. with unidirectional magnetic fields. In some cases, implanted magnets were used. The reports on these experiments stated that the treated patients lived a few weeks longer than normally expected and concluded that further work was justified.

The best reported results were obtained by Dr. Kenneth A. MacLean of New York City, who used a several kilogauss, very low frequency pulses, unidirection field generating electromagnet. Dr. MacLean treated several terminal patients by subjecting the entire body to a burst of the large, unidirectional magnetic fields every few seconds. The published reports indicate the patients lived months longer than they otherwise would have.

Work on the present invention has led the inventor to believe that one of the main reasons for the beneficial effects of Dr. MacLean's pulses field technique resides in the effects of the leading and trailing edges of the magnetic pulses producing shocks which causes some tumbling of the magnetically responding intercellular elements. In addition, the present inventor has determined that the transient phenomena of the rise and fall periods of the magnetic pulses would also generate a change in the nucleus to shell bioelectric bipolar voltage potential, thus causing additional cellular disturbances for at least their time durations.

On the other hand, problems inherent in Dr. MacLean's technique and absent in the present invention are the costly massive bulk of the equipment used including banks of storage batteries and the use of magnetic field strengths substantially above 550 gauss. The latter may be a problem since it has recently been established that 550 gauss is the threshold of normal cell tolerance for magnetic field exposure, and that when this level is exceeded normal cell changes occur, which may lead to possible undesired side effects with long term use.

SUMMARY OF INVENTION

Accordingly, it is an object of the present invention, to provide an improved method and apparatus for treating malignant cells and tumors.

Further, it is an object of this invention to provide a non-invasive, highly versatile, compartively safe and effective alternative or supplemental method and apparatus to the medical professional for treating carcinoma and sarcoma tumors with major emphasis on those which respond poorly to existing methods of treatment or those for which present methods are limited due to undesirable side effects.

To achieve this and other objects, the present invention resides in externally applying a sinusoidal magnetic field to the malignant cells. Preferably, this alternating magnetic field is a low frequency field (e.g. below 500 Hz) having a field strength of between 50 gauss and 550 gauss. By applying such a field which contains and sweeps most of the frequency components present in cellular pulse trains and bioelectric voltage excursions, it has been found that mitosis is inhibited or reduced in the malignant cells while normal cells remain relatively unaffected.

BRIEF DESCRIPTION OF THE DRAWINGS

Embodiments of the invention will now be described in detail with reference to the accompanying drawings.

DETAILED DESCRIPTION OF THE INVENTION

Figure 1:
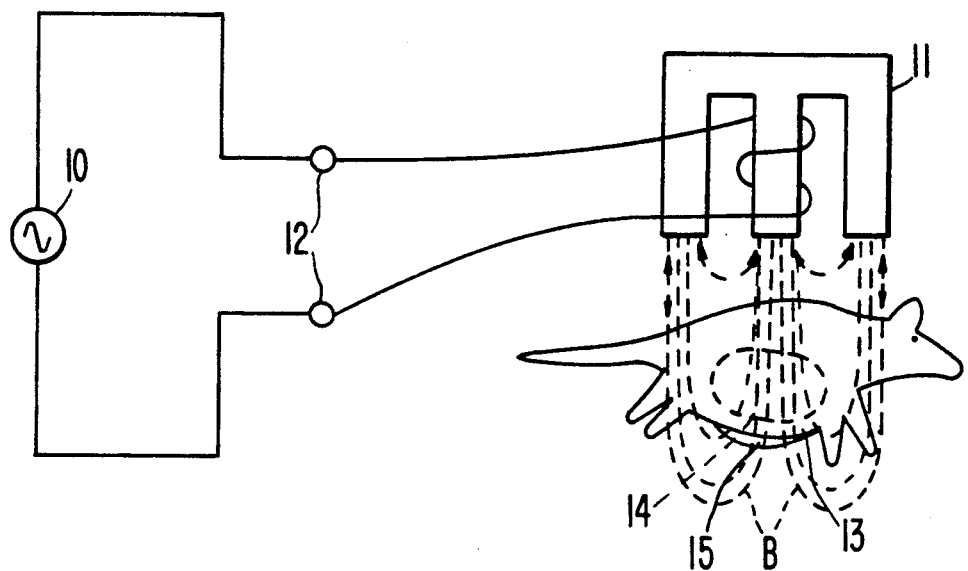
FIG. 1 is a representation of a ferrite core demagnetizing field coil positioned to treat a small mammary carcinoma extending inward less than one and one-half inches from the alternating field generator.

Before a detailed description is given of preferred embodiments, a brief discussion will be given of some of the principles involved in this invention.

The conception of this invention was biased on a number of postulates. In particular, it was assumed that at least some types of malignant cells would show more intense (while still slight) magnetic properties than normal cells when placed in a strong magnetic field. It was further assumed that is placed in a sinusoidal, demagnetizing type of magnetic field, the cell elements with slight magnetic properties would align themselves with the alternating magnetic lines and tend to lock themselves in synchronization or resonance with the alternating field, providing the magnetic field frequency and cellular magnetic responding elements' physical maneuvering capabilities were compatible, thus, it was theorized that much stronger tumbling, spinning, and possibly destructive disturbances would occur in the ambient environments of malignant human type cells than would occur to those of the less magnetic normal cells.

In particular, it appears form the inventor's studies that the strong alternating magnetic field disturbances severely affect, at least, the second step of mitosis wherein the chromatids arrange themselves in upper and lower equatorial planes of the spindle, each spinning and trying to align one end with the end of an adjacent chromatid. As alignment of two adjacent chromatids begins to occur, the spinning continually slows down and comes to a stop when the two chromatids reach perfect alignment. Each chromatid then splits to form the matched pair which is required for chromosomes. Since all the chromatids in both equatorial planes must complete the alignment and splitting process before mitosis can proceed, intermittently applied wave type tumbling forces which disturb chromatid alignment would inhibit or reduce cell reproduction. Accordingly, development of the invention proceeded on this concept to obtain significant disturbances to mitosis in the malignant cells without adversely affecting normal cells.

With regard to the inventor's theories regarding this difference in magnetic responsiveness of normal and malignant cells, it is noted that a technique has recently been developed using magnets to draw cancer cells from bone marrow which has been extracted from the body and then returning the remaining healthy marrow to the body. The technique relies on magnetic beads which clean the bone marrow after it is removed from the body by magnetically attracting the cancerous cells and leaving behind the healthy marrow. The malignant cells had, in these medically documented cases, actually responded as magnetic substances while the normal cells remained relatively non-magnetic. This is considered as scientific and factual support evidence for, at least, some types of cancers to one of the postulates upon which this invention was based.

A second postulate for the present invention is based on intra and intercellular electrical characteristics as a function of cell activity. A comparison of normal and some malignant cells indicates malignant cell activity can be called vicious in intensity and high in speed. The intracellular high speed is evident in the rate of mitosis and the rapidity at which the precise requirements of each of the four sequential steps of cell reproduction are performed. Evidence of cummulative intercell activity is apparent in the manner in which these cells destroy adjacent normal cells cutting through even blood vessels. The thermal activity of a small tumor of mammary carcinoma cells is such that heat is generated which elevates the surface skin temperature by roughly two degrees. It is known that cellular activity is generated by intracellular bioelectric voltage changes or in response to intercellular bioelectric voltage changes which exhibit pulse train spike patterns in the millisecond time regions with voltage excursion swings from roughly minus eighty millivolts (membrane to nucleus) to roughly plus twenty millivolts. The cellular fluids involved are conductive solutions containing positive Potassium and Sodium ions with negative Chlorine ions which are exchanged during the bioelectric voltage swings. Thus, an analysis by the inventor of the rise, fall and duration time periods of intracellular pulse train patterns gave an indication of cellular element mobility. Further analysis of photographs of oscilloscope traces of these voltage pulse train patterns (with the microprobe actually penetrating the cell) published by the Neuropsychology Research Lab., Sepulveda, Calif. and the Brain Research Institute, U.C.L.A. indicated many cells can complete an action cycle in two milliseconds or at a five hundred hertz frequency. Thus, it appears that the malignant cellular elements which have stronger magnetic substance characteristics than normal cells would be disturbed from their natural rhythms by a strong low frequency sinusoidal magnetic field while the natural rhythm of normal cells remains relatively unaffected. In addition, the magnetic flux lines cutting through the conductive ionic cellular fluids would generate an alternating voltage which should disturb ion transfer, particularly on the highly active malignant cells.

Accordingly, from the above discussion, it can be seen that a number of factors exist which appear to explain why the application of a strong, low-frequency sinusoidal magnetic field have brought about regression or destruction of malignant cells without injuring normal cells. It should be noted at this point that the above-discussed postulates are the inventor's theories as to why the present invention, which will be described hereinafter, works successfully in the experiments conducted. They are offered here solely to assist in understanding the invention since, as will be shown, malignant cells treated in accordance with the present invention certainly do seem to have mitosis significantly disturbed whereas the functioning of normal cells remains relatively unaffected. Thus, the malignant cells seem to respond to the strong low-frequency sinusoidal magnetic fields as would be expected under the inventor's theories. However, it may be that disturbances other than those theorized above are actually caused by the alternating magnetic field to bring about or at least contribute to the desired results which the inventor has achieved. Accordingly, the present invention is not intended to be limited to these theories since, as is often the case, significant practical results can be obtained and utilized by practicing certain methods without fully understanding all of the physical reasons as to exactly why the techniques are successful.

Turning now to a description of preferred embodiments of the present invention, a first embodiment for treatment of a carcinoma near the skin surface is shown in FIG. 1. In particular, a ferrite core demagnetizing field coil (shown in FIG. 1) is positioned over the lump 15 on the breast surface caused by the previously medically implanted small carcinoma tumor 14 in a female animal breast 13. This coil 11 receives alternating current power through terminals 12 from adjustable A.C. source 10. The frequency components contained in readily available 50 or 60 hertz sinusoidal power lines remarkably cover the range of transcient phenomena frequency components contained in the previously mentioned cellular generated pulse trains. The sinusoidal power line waves contain most of the high frequency (short time) components of the cellular pulse trains below the half power point (0.707 of peak value) and most of the low frequency (long time) components of the cellular pulse train between the half power points and peak value. Thus, a conventional Variac or Powerstate plugged into a 50 or 60 Hz power line makes a suitable adjustable A.C. source 10 after initial calibration with the particular coil 11 being used. The resulting alternating magnetic field B will contain the desired sweep frequency component characteristics to irradiate the carcinoma tumor 14 with an alternating magnetic field B of at least 50 gauss which is roughly the minimum field strength threshold level which, when applied for at least five minutes a day produced beneficial results. The preferred field strengths at the tumor are 150 to 250 gauss applied for at least 15 minutes a day. The adjustment of the variable power source 10 is determined by the tumor size, its innermost depth and spacial characteristics of the magnetic field B, determined by the particular coil 11 being used. For example, if the area of the carcinoma tumor 14 is roughly 0.5 inches in diameter with its farthest point from the field generator 11 being one and one half inches, and if the coil 11 is similar to a modified (for duty cycle and safety reasons) bulk tape eraser, such as Realistic #44-232, then the adjustable power source 10 would be at full line voltage with the coil 11 drawing its maximum of 4 amperes. The spacial characteristics of field B had been determined previously by moving the probe of a conventional A.C. Gaussmeter through the field B and plotting the field strengths as a function of distance from the coil 11. Under these conditions, the one and one-half inch edge of the malignant tumor 14 is at the 120 gauss point, well above the 50 gauss minimum, and the surface normal cells are at lower than the 550 gauss level, above which changes in normal cells have been reported. Thus, the conditions are just barely within the desired parameter limits to achieve the aims of this invention. If the edge of the same tumor 14 was 0.75 inches from the surface, then the adjustable power source should be set at slightly above the one-half power (2 amp) level to place the edge at the preferred 150 gauss level.

It was noted while work was in progress on this invention, that cancers which responded to conventional radiation therapy also responded to magnetic field irradiation and without the usual radioactivity caused side effects, when the roughly 50 gauss minimum was exceeded and particularly well above the preferred 150 gauss level. The 550 gauss maximum mentioned is in the interests of conservativeness and safety. Thus, higher gauss levels could be used, but this might bring about other undesired affects on normal cells.

The system described in FIG. 1 is directed toward the treatment of relatively small areas which are contained between the skin surface and a particular coil design which has limited field depths. The Realistic #44-232 coil described previously is only one example of such a coil, and it must be pointed out that the Realistic #44-232 was modified not only to improve its intermittent duty limitations but primarily to eliminate the potentially very dangerous 1,500 gauss to 600 gauss field density gradient contained in the area abutting the coil base and extending outward roughly ⅜ of an inch. In this region, nonmagnetic material such as copper and aluminum vibrate appreciably (even a penny or handful of coins) and quickly become eddy-current heated. Thus, attempts to treat basal cell and squamous cell carcinomas, commonly known as skin cancers, with a readily available, small, hand held tape eraser without safety modifications could result in a number of serious problems. Specifically if plugged directly into line power and held against a lesion on the cheek without any protective measures the high density field created by the Realistic #44-232 coil will shake adjacent metallic fillings in teeth and may generate enough heat and thermal expansion in large fillings to crack teeth. In a similar manner if held on the chest over an implanted pacemaker or pacemaker wires, very probable catastrophic pacemaker failure may result. In general, it may be said that very high density alternating magnetic fields usually cause undesired vibrations, of varying degrees, in implanted metallic structures which are classified as nonmagnetic and always generate eddy current temperature elevation which may have serious consequences. It should be emphasized that the combination of the common beliefs that all magnetic fields are safe, that all nonmagnetic materials are always nonmagnetic and the innocent appearance of a small hand held demagnetizer, such as the Realistic #44-232 coil which in reality, generates insidiously high density magnetic field areas, can have serious, if not fatal, consequences.

Accordingly, if a coil such as the Realistic #44-232 coil having a strong localized field (i.e., well over 500 gauss) at its immediate coil base is used, an appropriate spacer (in this case approximately ⅜ of an inch) should be inserted between the coil base and the skin to prevent injury. This will serve to limit the field actually reaching the skin and the tumor to the desired range of 50 to 550 gauss (or more preferably to 150-250 gauss). Of course, an alternate to this is to utilize a coil having a sufficiently strong field without the highly localized field of the realistic #44-232 coil, such as a peripheral edge of one of the larger circular coils to be described in FIG. 2. Such circular coils provide a more uniform and deeper field without strong localization, and therefore, are generally preferable.

Figure 2:
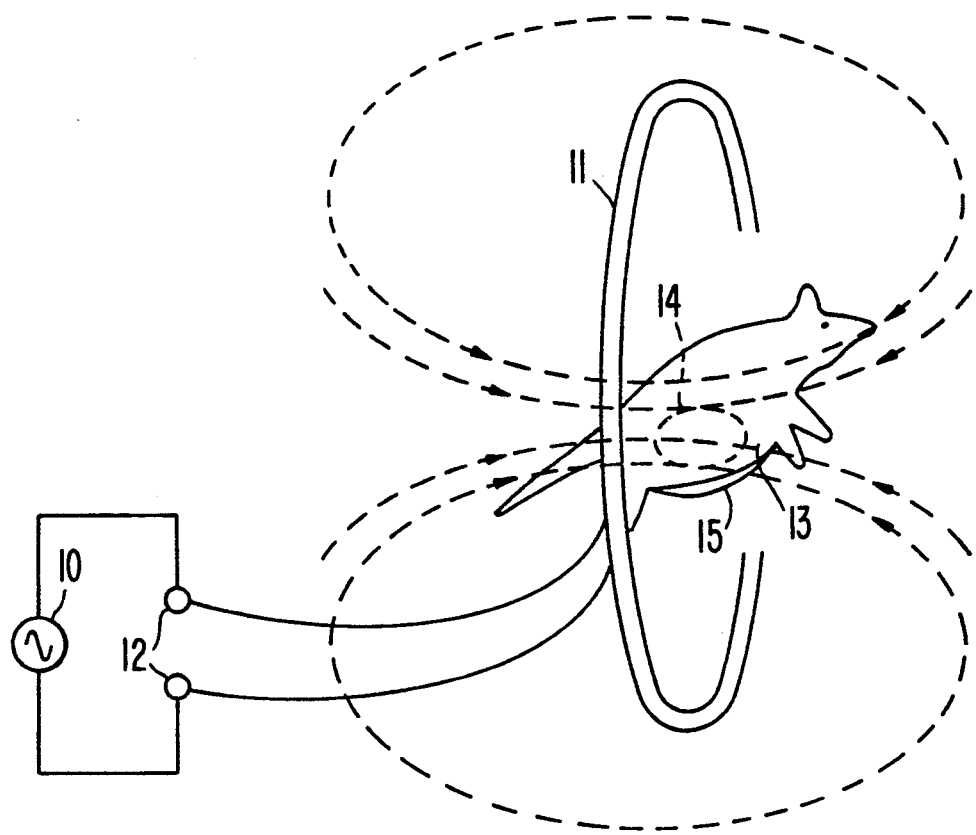
FIG. 2 is a representation of a demagnetizing field coil positioned to treat a large mammary carcinoma extending inward less than four inches from the field coil.

FIG. 2 shows an embodiment of the invention, directed toward the treatment of larger and/or more distant tumors 14 than those discussed for FIG. 1. The air core circular wound demagnetizing field coil 11 is positioned around the malignant areas or may be moved outward to place the approximate center of the tumor 14 on the imaginary center of the coil 11. If coil 11 in an RCA #205W1 Degausser which is fed through terminals 12 from adjustable power source 10 then at full line voltage, coil 11 draws 3 amperes and a spacial characteristic analysis of the magnetic field (as previously described for FIG. 1) indicated a tumor 14 or tumors 14A contained in an imaginary spheroid (envelope) bounded by the 12 inch diameter of the coil 11 and extending slightly more than 4 inches in both directions of the field 14 axies would be irradiated with the preferred field strengths to achieve desired results an in a relatively uniform field. In practice, a single RCA #205W1 acting as coil 11 requires air cooling supplied by a fan, not shown, when operating at full power for the required periods. For this reason, two or three such coils taped together and wired as a cylindrical coil provide more efficient heat dissipation since each coil draws one amp to produce roughly the same field as a single coil operating at 3 amps. The low cost 12 inch diameter coil 11 was selected for convenience and suitability for the application described. It should be noted that other coils and combinations are more effective for certain particular situations, as discussed in FIG. 3.

Figure 3:
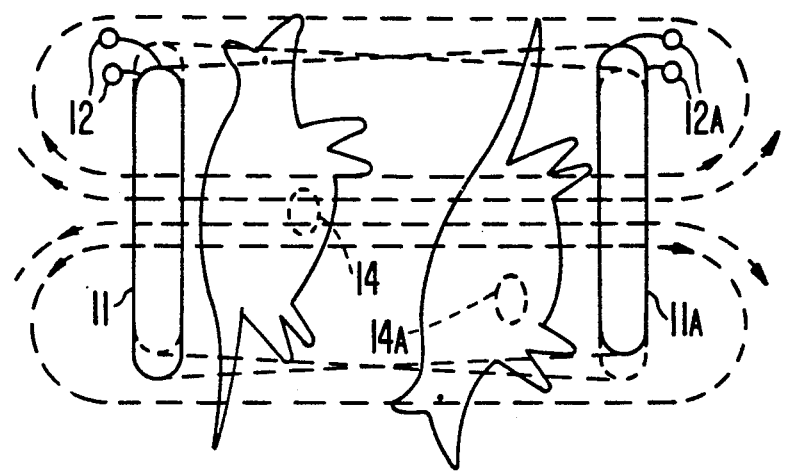
FIG. 3 is a representation of two demagnetizing field coils oriented to provide additive magnetic fields and positioned to treat multiple malignancies between the peripheries of the field coils.

FIG. 3 shows an embodiment of the invention directed toward the treatment of widely separated multiple tumors (as in metastasis). In FIG. 3, tumor 14B is near the coil 11, tumor 14 is deep in the center and tumor 14A is near the coil 11A. Since these are totally contained within the cylindrical volume between two inch coils, coil 11 positioned on the front of the treated area and coil 11A placed on the back, can be similar to coil 11 as described in FIG. 2. The coils 11 and 11A are oriented to be field additive and function electromagnetically as two halves of one coil. Therefore, a very uniform magnetic field B with small density variations is generated within the cylindrical volume between the coils 11 and 11A when the power through terminals 12 is supplied from power source 10. However, since coils 11 and 11A are physically two advantageously different coils, they can be independently moved or offset as shown in the dotted portions of FIG. 3. Coil 11 has been moved upward and coil 11A downward to produce a skewed magnetic field. In practice coil 11 could have a 12 inch diameter and coil 11A a smaller or larger diameter to produce a frustroconical field, if such a field were desired.

Figure 4:
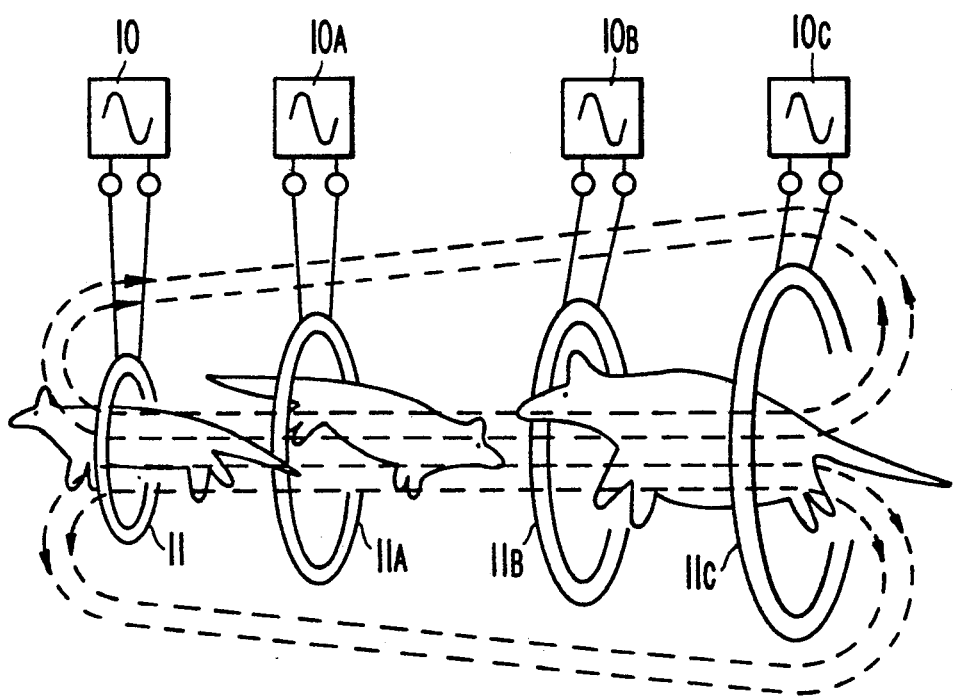
FIG. 4 is a representation of a multiple coil arrangement in accordance with the present invention to provide a tailored magnetic field for treating an elongated area.

FIG. 4 is a representation of a plurality of substantially air core coils 11, 11A, 11B, 11C, arranged to generate an elongated alternating magnetic field. The coils are individually positioned by gooseneck type holders, not shown, and thus supported to generate the particular desired magnetic field patterns. In this manner, a wide variety of unique magnetic patterns with relatively uniform or variable densities become possible. This method in conjunction with the previously discussed methods of magnetic field generation, may be particularly useful in the treatment of lymphosarcoma tissue. Lymphosarcoma is a disease which may start in any organ in a body, including any lymph node. The disease then spreads to other areas via blood or lymphatic channels. When bone marrow is primarily involved the elongated magnetic field technique discussed in FIG. 4 is particularly applicable.

The professional medical environment in the United States dictates that new methods for treatment of cancers undergo extensive animal evaluation prior to clinical evaluation on humans at specifically approved medical research centers. Accordingly, implementation of this invention was performed by treating human cancers implanted into pure bred Sprague-Dawley white rats and research grade mice as hosts. All animals were maintained under highly controlled laboratory conditions, such as housed in a sanitary, air conditioned room, properly fed and watered and all autopsies were performed by a certified pathologist. It is generally considered that what happens in the selected laboratory rats and mice in one day will correspond to similar human reaction in roughly 35 days. Therefore, one significant advantage of using such test specimens is that the test results can be obtained much more quickly and with more valid conclusions than is possible with human testing.

A wide variety of tests were conducted using the sinusoidal magnetic fields with structure such as described in FIGS. 1 and 2 using field strengths between 25 and 550 gauss. In particular, these tests were carried out on rats and mice implanted with either human Lymphosarcomas (Walker Strain) mammary Carcinomas or Gardner tumors. Testing was always conducted such that treatment began when the specimen had entered what was considered by Dr. Jasper ChenSee, a certified pathologist, to be a terminal stage. Each test group was divided so that half the specimens were treated while the other half remained untreated. Although many tests were conducted, only the particularly significant results will be set forth herein to illustrate the main advantages of the present invention.

Beginning with the testing of the mammary carcinomas, it should first be pointed out that breast carcinoma is the most common malignancy among women and has the highest fatality rate of all cancers affecting women throughout the world, and, correspondingly, one of the major areas of importance for treating cancer. For these tests, Walker Strain Carcinoma tumors were implanted in the breast of young adult female Sprague Dawley rats. After eight days, small tumors could be seen. After 10 more days, the tumors had developed to the acute stage and, in some cases, had increased the body size by almost 50 percent. Treatment was then begun.

Following the beginning of treatment, it was found that the untreated rats died within 10–12 days. On the other hand, when treated groups of rats were subjected to sinusoidal field strengths of 50 to 75 gauss for five minutes per day, 25 percent of the specimens had complete regressions within the 10–12 day period. Also, the remaining specimen showed significant reduction in tumor sizes during that period. Increasing the time to 15 minutes per day did not significantly improve upon these results.

More significantly, when specimen were subjected to field strengths of 150 to 250 gauss, it was found that approximately 80 percent of the test specimens had complete regression within the 10–12 day period. Test were conducted in the field duration time between five minutes per day and 15 minutes per day of exposure, and, the main difference that was found was that when the specimen were exposed to a longer period of time, regression generally occurred at a faster rate. In any event, it can be seen that the Walker Strain mammary carcinoma is apparently one type of cancer which appears to be quite responsive to magnetic treatment in accordance with the present invention.

Turning now to the Lymphosarcoma testing, the initial tests were conducted at 25 gauss for a minimum of five minutes per day. Based on this testing, minimal improvements in the order of improvements previously found in D.C. magnetic field treatment was found. For example, of a test sample of 18 rats, the nine treated rats lived, on the average, half a day longer than the nine untreated rats (noting that the untreated rats died within five to seven days). This half day improvement only corresponds to approximately two weeks in humans. Thus, the results are of limited significance. Increasing the time period of exposure to 15 minutes per day brought about no significant improvement on these results.

On the other hand, when the dosage increased to 50 to 75 gauss for five minutes per day, a considerable improvement was noted in the rats having lymphosarcoma. Specifically, although the untreated rats died within five to seven days, the treated specimen lived between 28 to 31 days. In each case, the rats remained mobile until their last two or three days. Thus, the treated specimens generally had close to a full month of mobile existence whereas the untreated rats generally had less than one week. This difference corresponds to approximately two years of a human's lifetime which is, obviously, a significant improvement.

Finally, tests were made with the Gardner tumor, which, like Lymphosarcoma, is an extremely lethal tumor which is generally considered to be incurable when it becomes malignant in the colon and has invaded the glandular system, progressively destroying these organs (as Adenocarcinoma). Although, unlike the walker Strain mammary carcinomas no complete regressions were obtained, as was the case with Lymphosarcoma, application of the techniques to the present invention did bring about a significant lengthening of the lifetime of the test specimens. Specifically, testing began with 50 to 75 gauss dosages for five minutes per day. Under these conditions, the treated mice lived between 21 and 23 days longer than the untreated mice (which died within 5 to 6 days after the beginning of testing). Thus, an extension of the lifetime on the order of two years in human terms were also obtained. Testing then continued within another group of mice being subjected to 150 to 550 gauss for 15 minutes per day. Under these conditions, substantially the same results were obtained as for testing five minutes per day using 50 to 75 gauss.

Although the present invention has been discussed with regard to testing on three particular types of cancer, the present invention is not intended to be limited to this since it is believed that a variety of other cancers are likely to respond to such treatment to varying extent. As can be seen from the above examples, the treatment was especially beneficial with the Walker Strain mammary Carcinomas since it led to complete regressions within a majority of the test specimen. On the other hand, although it did not bring about complete regressions in specimens having Lymphosarcoma or Gardner tumor, it did at least add significantly to the lifetime of the test specimens which otherwise died very quickly from these types of cancer. It is believed that, with further testing, it is likely that a number of other cancers will be found to respond to the treatment in accordance with the present invention under medical supervision, either along or in conjunction with other forms of treatment, to either increase the active lifetime of the patients or, in some cases, bring about complete regressions.

Also, although the present invention has been discussed in terms of using line frequencies of 50 to 60 Hz, higher frequencies could be used if desired. As noted earlier, the cells themselves have a certain cellular communicating frequency. Therefore, as long as frequencies used for treatment covering a majority of the high and low frequency components of the cellular communicating frequency, beneficial results are likely. Therefore, it would appear that at least generally frequencies up to 500 Hz, or even higher frequencies, would provide some beneficial results. However, because of its ready availability and the fact that it does cover most cellular frequency components very well, standard A.C. line frequencies of 50 or 60 Hz are used in the preferred embodiments of the present invention.

It should be clearly stated and emphasized, at this time, that the unique characteristics and startling (at least in this work) end results of the alternating electromagnetic fields described herein, cannot be equated in practice, to those of unidirectional permanent or pulsating magnets. Nor can conventional instrumentation (generally developed prior to about 1950) normally used to measure magnetic field strengths (also called flux density, field intensity or lines of force) of unidirectional fields be used to determine the field strengths of the alternating sinusoidal electromagnetic fields used in this invention.

The probe of a conventional flux density meter, when placed in a static magnetic field, measures the force exerted on a unit pole and displays the output as Oersteds, Maxwells, or Gauss, which are equivalent units. This type of field is in a quiescent state. Thus, the average and peak readings are always equal, in any particular spot in the field. In addition, since the field transfers or expends no net energy to stationary conductors or conducting fluids exposed to the field, no Eddy (also called Foucault) currents are generated. The published concensus of medical opinions indicates that exposure of humans or animals to this type of field, as strong as 20 kilogauss, for periods of a few minutes, produces no ill effects, other than a metallic taste in the mouths of people with metallic fillings and mild vertigo and nausea, in about a quarter of the cases of people exposed for longer periods of time. The most recently published medical study concluded that long period exposure to static magnetic fields of above 550 gauss produced changes in normal living cells but did not establish whether the change was beneficial or harmful.

When the probe of the conventional flux meter is placed in a unidirectional pulsating field, the pressure acting on the unit pole swings from zero to a maximum with a return to zero, then the cycle repeats. The forces acting on the unit pole are always in the same direction and displayed as the numerical average of duty cycle times flux density (during power on intervals). Peak flux density is determined by multiplying the reciprocal of duty cycle and average flux density. Accuracy is assured by calibrating the meter with a "standard" magnet.

Eddy currents generated in conductors or conductive solutions exposed to pulsating magnetic fields cause virtually no safety, vibration, or thermal problems because they are unidirectional and exist only during the driving power transition (rise and fall times) periods when small amounts of energy are transferred to conductors in the field which generate the Eddy currents, which then, in turn, generate relatively small amounts of heat.

Technical reports based on work with small numbers of people state that no ill-effects have been observed in people exposed to up to ten kilogauss fields or pulses for short periods of time.

When the probe of a conventional flux meter is placed in an alternating electromagnetic field, the probe output is zero because the force exerted on the unit pole during the positive half of the cycle is completely negated by the force exerted during the negative portion of the cycle and the to-and-fro numerical average is always zero, regardless of field flux density or field frequency. Thus, the unique characteristics of the constantly changing and sinusoidally reversing electromagnetic fields require special handling of the classical 19th century unidirectional magnetic field definitions of Oersted, and Gauss.

Moving magnetic fields transfer energy as electrical power to stationary conductors as a direct function of flux density. Therefore, small calibrated pick-up coils (operating below their saturation levels) were used to determine the average flux densities contained in the spacial geometry occupied by the coil by reading the induced voltage and/or current in the coil. Oscilloscope presentations of the induced voltages are also used to determine the frequency components contained in and swept by the magnetic flux excursions.

Prior to the late 1950's there were no commercially available single instruments capable of measuring field strengths and determining profiles of both unidirectional and alternating magnetic fields.

The numerous breakthroughs in semiconductor technology in the 1950's changed this situation.

A new "Hall Effect" probe which essentially consisted of a (tiny) thin wafer of semiconductor material with, back-to-back, diodes was developed. When placed in a magnetic field, its output voltage is proportional to a current passing through it times the field flux density perpendicular to it.

The resultant instrument was called a "Gaussmeter" by its manufacturer and readout is not in Oersteds or Maxwells but rather in Gauss.

The instrument is calibrated with a "standard" static field magnet of 1000 gauss. It equates force on a unit pole to a voltage, then reads directly proportional voltages. Thus, it one-step pedigrees back to classical physics for standardization.

When placed in an alternating magnetic field, the initial a.c. voltage generated in the probe by the alternating flux lines of force, is full wave rectified and the root-mean-square average voltage value (0.707 of peak) is used to determine the field strength at the small area occupied by the probe tip. Thus, more precision (i.e. accuracy and repeatability) than previously possible, is achieved.

This is the method used, with companion terms, to describe the fields used in this invention.

A pick-up coil attached to an a.c. voltmeter may be used for field monitoring and routine field set-up, if it is initially calibrated to correlate with a Hall-effect probe Gaussmeter.

The uniqueness of the characteristic of the alternating magnetic fields described herein and their influences on magnetic, paramagnetic material such as aluminum, an conductive fluids, are such that a complete separation is necessary from generally conceived "magnetic field" phenomena. For example, the general conceptions are, when placed in "magnetic fields" (1) ferromagnetic material is attracted and becomes a magnet itself; (2) paramagnetic material such as aluminum or copper do virtually nothing; (3) paramagnetic conducting fluids just polarize and do nothing else; and (4) a compass needle points to the north pole and remains so indefinitely until the compass is moved.

The actual scientific facts, however, are that, when placed in the "magnetic fields" of this invention:

(1) Ferromagnetic materials attempt to align themselves with the changing and reversing line of force, thus small objects tumble and shake violently whereas, large materials vibrate with violence and in addition, the materials become heated by the inductively generated Eddy currents. The materials also become demagnetized. This is the opposite of the above.

(2) Aluminum or copper do not do virtually nothing. They act instead as conductors in a moving magnetic field and as short-circuited turns in the secondary of a transformer. Thus, the generated voltages and Eddy current reactions to the moving field result in severe material vibration and temperature elevation. Energy is transferred, absorbed and expended.

(3) In paramagnetic conducting fluids small voltages and Eddy currents are similarly generated. These result in stirring type fluid motion and temperature elevation.

(4) A compass needle would not become quiescent and point to the N pole, it would instead quickly become demagnetized, while shaking and vibrating violently, in three axes even after complete destruction as a compass.

The examples presented are intended to show that the conclusions and opinions in published reports under the general heading "Biomagnetic (or Bioelectric Effects of Magnetic Fields)" relate only to the static or pulsed fields which the authors used and are invalid and not applicable to the alternating electromagnetic fields used in this disclosure.

The influences on objects subjected to static or pulsed unidirectional fields are very similar, the only differences being in the leading and trailing edge transient phenomena, whereas the same objects subjected to sinusoidal alternating field influences produce such different results and reactions, as the previous examples indicate that there can be no reconciliation or equating of the results of different field influences on paramagnetic substances including those in living tissue and cells, both normal and malignant.

Figure 5:
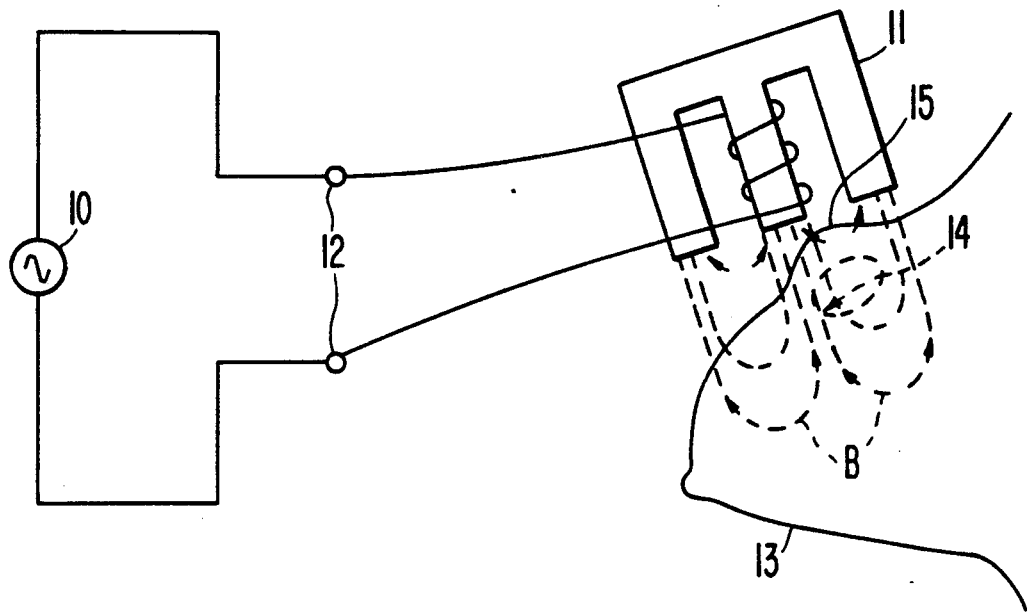
FIGS. 5 to 8 show how the coil arrangements illustrated in FIGS. 1 to 4 could be applied to tumors in humans.
Figure 6:
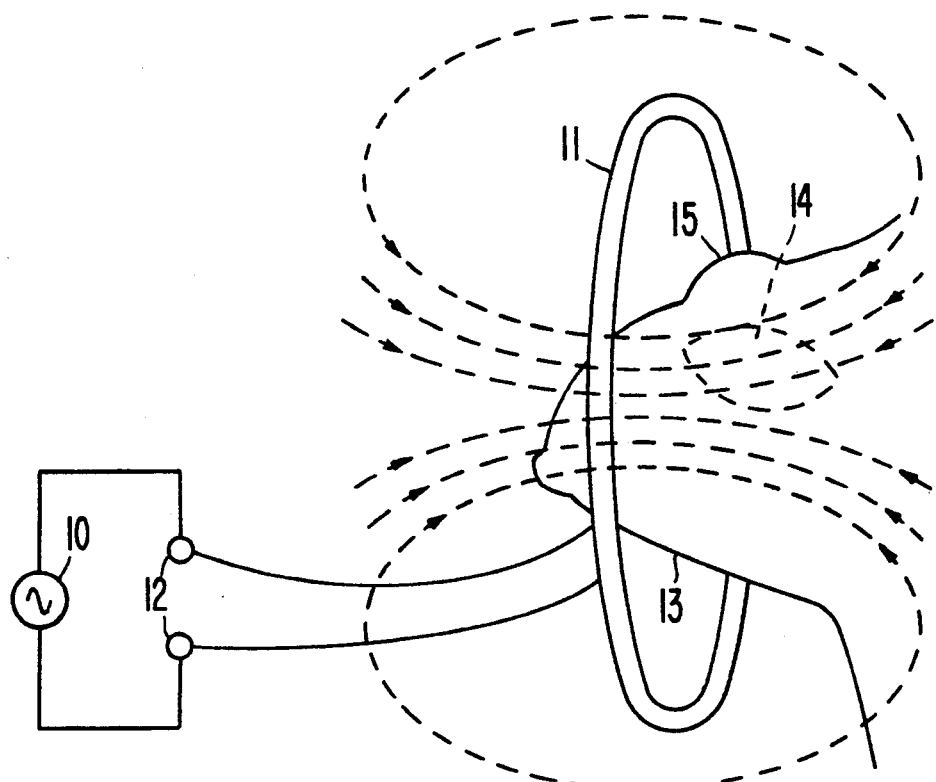
Figure 7:
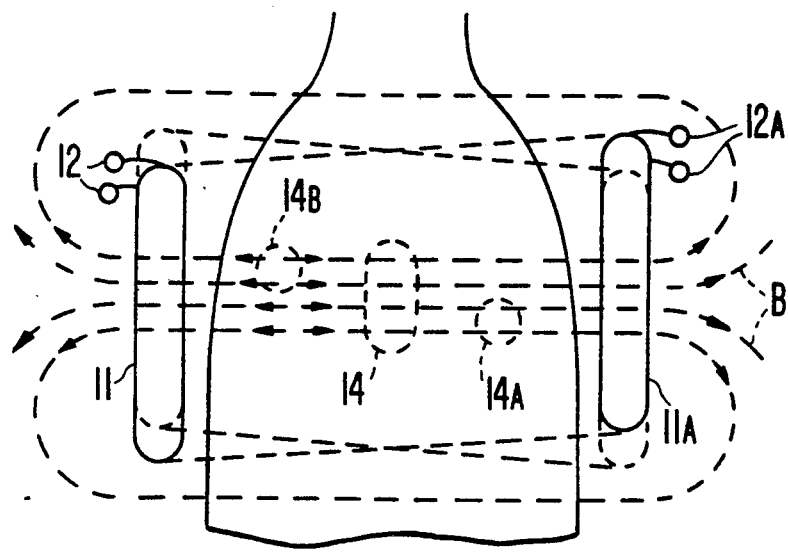
Figure 8:
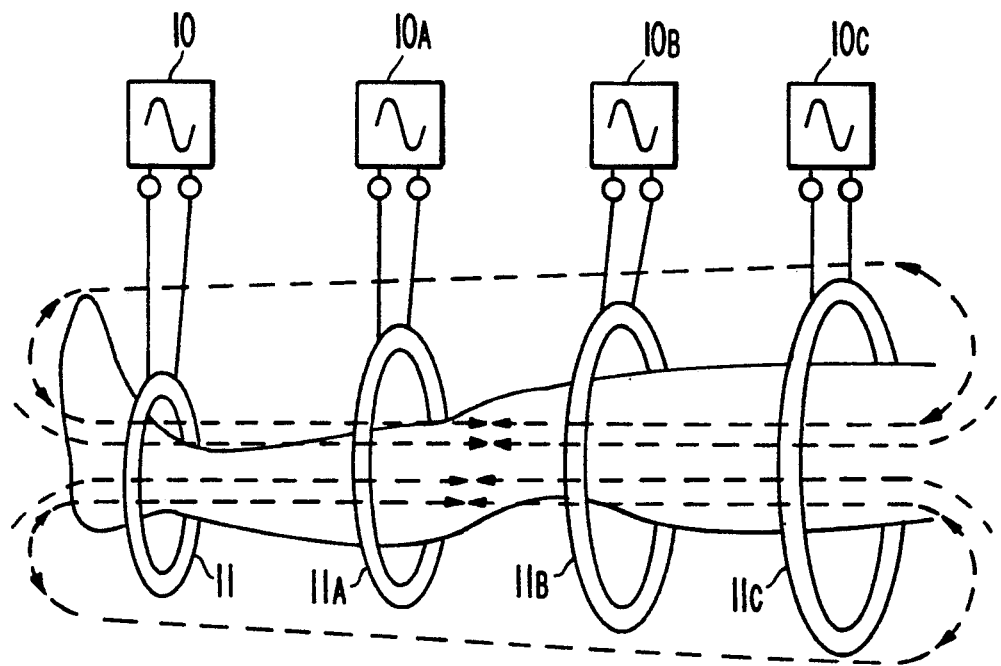

The above discussion has related to the application of the invention to laboratory test animals on which tests were conducted by the inventor. FIGS. 5, 6, 7 and 8 are suggested for future experimental work as to how the various coil arrangements of FIGS. 1, 2, 3 and 4 might be applied to cancers in human patients to establish whether the cited animal utility might be applicable to humans as well. Specifically, FIGS. 5 and 6 illustrate suggested coil arrangements for experimental studies of breast tumors, FIG. 7 illustrates suggested coil arrangements for experimental studies of deep seated tumors inside the chest, and FIG. 8 illustrates suggested coil arrangements for experimental studies along a leg. It is noted that the applicant has not tried the invention on humans.

It is to be understood that the above-identified arrangements are simply illustrative of the application of the principles of this invention. Numerous other arrangements may be readily devised by those skilled in the art which embody the principles of the invention and fall within its spirit and scope.

I claim:

1. A method for treating malignant cells in living tissue comprising:
externally applying a sinusoidal magnetic field having a field strength of between 50 and 550 gauss throughout the malignant cells to inhibit mitosis of said malignant cells.

2. A method according to claim 1, wherein the field strength of said sinusoidal magnetic field is between 150 and 250 gauss.

3. A method according to claim 1, wherein said field is applied to said malignant cells for substantially at least 5 minutes per day for a plurality of days.

4. A method according to claim 3, wherein said malignant cells comprise a malignant Gardner tumor.

5. A method according to claim 3, wherein said malignant cells comprise a malignant Carcinoma tumor.

6. A method according to claim 3, wherein said malignant cells comprise a malignant Sarcoma tumor.

7. A method according to claim 1, wherein said malignant cells comprise a malignant Carcinoma tumor.

8. A method according to claim 1, wherein said malignant cells comprise a malignant Gardner tumor.

9. A method according to claim 1, wherein said malignant cells comprise a malignant Sarcoma tumor.

10. A method according to claim 1, wherein the frequency of said field is substantially 60 Hz.

11. A method according to claim 10, wherein the field strength of said sinusoidal magnetic field is between 150 and 250 gauss.

12. A method according to claim 10, wherein said field is applied to said malignant cells for substantially at least 5 minutes per day for a plurality of days.

13. A method according to claim 1, wherein said sinusoidal magnetic field is applied by a demagnetizing field coil coupled to an adjustable alternating current source, wherein adjustment of the alternating current source is determined by factors including the size of a tumor containing the malignant cells, an innermost depth of the tumor within the living tissue and spacial characteristics of a magnetic field generated by the coil.

14. A method according to claim 13, wherein said coil is a ferrite core demagnetizing field coil.

15. A method according to claim 13, wherein said spacial characteristics of the magnetic field are determined by moving a probe of an AC gaussmeter through the magnetic field and plotting field strengths as a function of distance from the coil.

16. A method according to claim 13, wherein a spacer is inserted between said coil and said living tissue to prevent direct contact between the coil and the living tissue.

17. A method according to claim 1, wherein said sinusoidal magnetic field is applied by an air core circularly wound demagnetizing field coil positioned to surround the living tissue containing the malignant cells.

18. A method according to claim 1, wherein said sinusoidal magnetic field is applied by a first coil located on one side of said living tissue and a second coil located on an opposite side of said living tissue.

19. A method according to claim 18, wherein said first and second coils are located to be substantially parallel to one another.

20. A method according to claim 18, wherein said first and second coils are circular and are arranged to be parallel to one another so that said living tissue is located in a cylindrical volume formed between the first and second coils.

21. A method according to claim 20, wherein said first and second coils are oriented to be field additive to function electromagnetically as two halves of one coil to provide a substantially uniform magnetic field B within said cylindrical volume.

* * * * *